(12) United States Patent
Jacobsen et al.

(10) Patent No.: US 7,603,153 B2
(45) Date of Patent: Oct. 13, 2009

(54) MULTI-ELEMENT PROBE ARRAY

(75) Inventors: Stephen C. Jacobsen, Salt Lake City, UT (US); David P. Marceau, Salt Lake City, UT (US); Shayne M. Zurn, Salt Lake City, UT (US); David T. Markus, Salt Lake City, UT (US)

(73) Assignee: Sterling Investments LC, Salt Lake City, UT (US)

( * ) Notice: Subject to any disclaimer, the term of this patent is extended or adjusted under 35 U.S.C. 154(b) by 134 days.

(21) Appl. No.: 11/637,508

(22) Filed: Dec. 11, 2006

(65) Prior Publication Data

US 2007/0167815 A1    Jul. 19, 2007

Related U.S. Application Data

(60) Provisional application No. 60/749,777, filed on Dec. 12, 2005, provisional application No. 60/749,873, filed on Dec. 12, 2005.

(51) Int. Cl.
*A61B 5/00* (2006.01)
*H01R 43/00* (2006.01)

(52) U.S. Cl. .................. 600/372; 600/310; 600/345; 607/116; 29/825

(58) Field of Classification Search .............. 600/300, 600/372; 607/116
See application file for complete search history.

(56) References Cited

U.S. PATENT DOCUMENTS

| | | | |
|---|---|---|---|
| 3,337,838 A | 8/1967 | Damiano et al. |
| 3,601,759 A | 8/1971 | Barker |
| 4,132,461 A | 1/1979 | Jacques et al. |
| 4,203,650 A | 5/1980 | Millet et al. |
| 4,369,104 A | 1/1983 | Beckley |
| 5,270,485 A | 12/1993 | Jacobsen |
| 5,599,615 A | 2/1997 | Swift et al. |
| 5,610,747 A | 3/1997 | Jacobsen |
| 5,861,662 A | 1/1999 | Candelore |
| 6,020,747 A | 2/2000 | Bahns et al. |

(Continued)

FOREIGN PATENT DOCUMENTS

GB    2039421    8/1980

(Continued)

OTHER PUBLICATIONS

Patterson, William et al. "A microelectrode/microelectronic hybrid device for for brain implantable neuroprosthesis applications": IEEE, Oct. 2004, pp. 1845-1853, vol. 51, No. 10.

(Continued)

*Primary Examiner*—Lee S Cohen
(74) *Attorney, Agent, or Firm*—Thorpe North & Western LLP

(57) ABSTRACT

A multi-element probe array suitable for sensing or stimulating is disclosed. In one embodiment, the multi-element probe array includes a plurality of microfibers extending longitudinally and oriented substantially parallel to form a bundle. Probe elements are defined by a first subset of the microfibers displaced in a forward direction alone the longitudinal axis relative to spacer elements defined by a second subset of the microfibers. Interface elements and communication elements are disposed on the probe elements.

25 Claims, 4 Drawing Sheets

U.S. PATENT DOCUMENTS

| | | | |
|---|---|---|---|
| 6,110,354 | A | 8/2000 | Saban et al. |
| 6,128,527 | A | 10/2000 | Howard, III et al. |
| 6,289,187 | B1 | 9/2001 | Swift et al. |
| 6,330,466 | B1 | 12/2001 | Hofmann et al. |
| 6,334,856 | B1 | 1/2002 | Allen et al. |
| 6,444,102 | B1 | 9/2002 | Tucci et al. |
| 6,462,398 | B1 | 10/2002 | Jojiki |
| 6,515,346 | B1 | 2/2003 | Kemeny |
| 6,740,214 | B1 | 5/2004 | Dobson et al. |
| 6,794,984 | B2 | 9/2004 | Komatsu |
| 6,829,498 | B2 | 12/2004 | Kipke et al. |
| 6,851,980 | B2 | 2/2005 | Nelson et al. |
| 6,892,438 | B1 | 5/2005 | Hill et al. |
| 6,924,439 | B1 | 8/2005 | Bonni et al. |
| 6,946,851 | B2 | 9/2005 | Lee et al. |
| 6,953,347 | B2 | 10/2005 | McGrath et al. |
| 6,993,392 | B2 | 1/2006 | Nicolelis et al. |
| 7,010,356 | B2 * | 3/2006 | Jog et al. .................... 607/116 |
| 7,333,699 | B2 | 2/2008 | Jacobsen et al. |
| 2004/0080056 | A1 | 4/2004 | Lim et al. |
| 2004/0125515 | A1 | 7/2004 | Popovich |
| 2005/0029009 | A1 | 2/2005 | Swift et al. |
| 2005/0029646 | A1 | 2/2005 | Kuzawinski et al. |
| 2005/0143790 | A1 | 6/2005 | Kipke et al. |
| 2005/0159028 | A1 | 7/2005 | Sweetland et al. |
| 2005/0202695 | A1 | 9/2005 | Sweetland et al. |
| 2005/0230795 | A1 | 10/2005 | Furuyama et al. |
| 2006/0039660 | A1 | 2/2006 | Henze et al. |
| 2007/0142714 | A1 * | 6/2007 | Shumate et al. ............. 600/300 |

FOREIGN PATENT DOCUMENTS

| | | |
|---|---|---|
| JP | 2004237077 | 8/2004 |

OTHER PUBLICATIONS

Normann, "Sight restoration for individuals with profound blindness", www.bioen.utah.edu/cni/projects/blindess.htm, Sep. 21, 2005, pp. 1-21.

"LSI Announces Wire-Bond Advance" pp. 1-2.

Brunner et at., "Advanced wire bond looping technology for emerging packages", SEMI Technical Symposium; Innovations in Semiconductor Manufacturing, 2004, pp. 1-8.

Karnezos et al. 3D Packaging Promises Perfomance, reliability Gains with Small Footprints and Lower Profiles, www.cipscalereview.com, Feb. 2005, pp. 1-6.

Chylak et al. "Overcoming the key barriers in 35 umPitch wire bond packaging: probe, mold, and substrate solutions and trade-offs" SEMI/IEEE, 2002, pp. 1-6.

ESEC "25um fine pitch solution", 2002, pp. 1-3.

ASE Kaohsiung, "CSP Leadless LGA", pp. 1-5.

Brunsting et al. "Enhanced optical performance for small form factor LC connectors": Panduit Corp., pp. 1-5.

Hayes, Jim "Connector types and terminology": Power and Integrated Building Systems, Editorial, pp. 1-2.

Allan, "Twist-pin concept increases miniature connector reliability" Electronic Design, The authority on emerging technologies for design solutions freescale.com pp. 1-2.

Bell, "Carpenter breaks barrier with nano-miniature connector specification", Mar. 9, 2005, pp. 1-3. Columbus Federal Voice. pp. 1-3.

Z-Axis Connector Company "Miniature Electronic Connectors": pp. 1-11.

Glenair MIL-DTL-32139 Nanominiature Connectors "Single row metal shell pigtails (M32139/01 & 02)": www.glenair.com, 2005, pp. 1-2.

Nano Line - NJS Microminiature, ITT Industries, www.ittcannon. com, p. L-14.

Nano Line - Strip-NT Microminiature, ITT Industries, www.ittcannon.com, p. L-15.

* cited by examiner

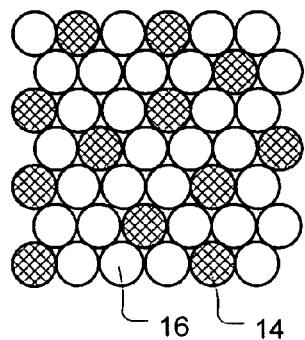
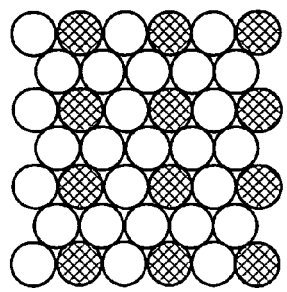
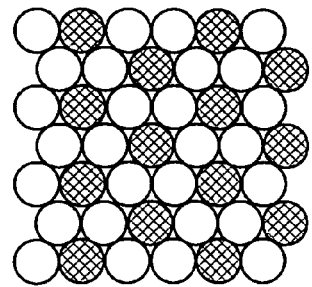
*FIG. 3*  *FIG. 4*  *FIG. 5*
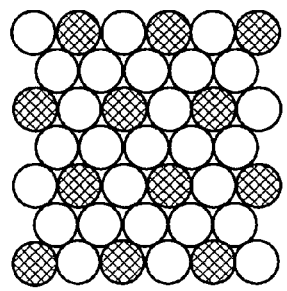
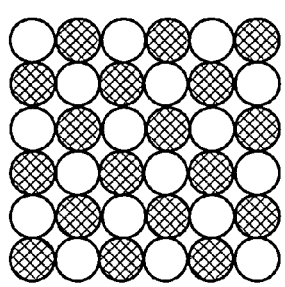
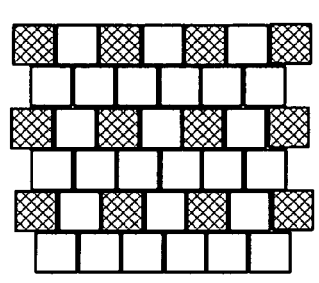
*FIG. 6*  *FIG. 7*  *FIG. 8*
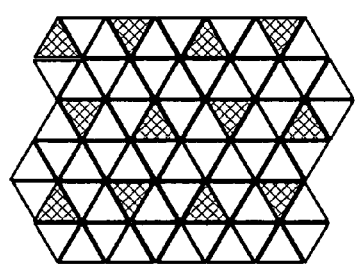
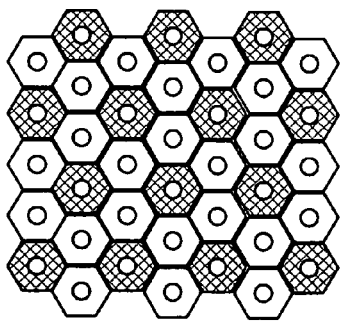
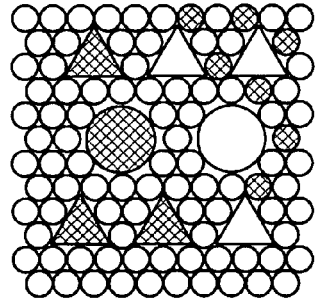
*FIG. 9*  *FIG. 10*  *FIG. 11*

MULTI-ELEMENT PROBE ARRAY

This application claims the benefit of U.S. Provisional Patent Application Ser. No. 60/749,777, filed Dec. 12, 2005, entitled "Ultra-High Density Electrical Connector" and U.S. Provisional Patent Application Ser. No. 60/749,873, filed Dec. 12, 2005 entitled "Multi-Element Probe Array," each of which is incorporated by reference.

BACKGROUND OF THE INVENTION AND RELATED ART

Various types of probes have found applications in chemical sensing, electronics testing, and medicine. Medical applications raise particularly challenging demands on a probe to be used for sensing or stimulation. For example, probes intended for use in interfacing directly to human tissue present several conflicting requirements. On one hand, it is desirable that a probe be quite rigid and strong so that it can be pushed through human tissue without breaking or deforming. On the other hand, it is desirable that a probe be very small, to minimize tissue damage, and flexible, so that is can move with the tissue into which it is embedded to avoid tearing.

In general, placement of probes into human tissue, such as the brain or a nerve has required a skilled surgeon to carefully position electrodes one by one at desired locations. This process is difficult and time consuming, and mistakes can lead to injury to the subject. Single probes are also difficult to fix in position without causing injury.

Probe arrays are known which provide for multiple connection points. Typically, these probe arrays are manufactured using silicon planar technology. The resulting arrays suffer from several drawbacks. The individual probe elements are brittle and relatively large compared to the size of nerve endings. Additionally, known probe arrays have relatively widely spaced probe tips, providing lower spatial resolution than desired.

SUMMARY OF THE INVENTION

The present invention includes multi-element probe arrays which help to overcome problems and deficiencies inherent in the prior art.

In accordance with the invention as embodied and broadly described herein, a multi-element probe array can be used for sensing or for applying a stimulus. The probe array includes a plurality of microfibers extending longitudinally and oriented substantially parallel to each other to form a bundle. A first subset of the plurality of microfibers define probe elements, and a second subset of the plurality of microfibers define spacer elements, wherein the front ends of at least one of the probe elements are displaced in a forward position along the longitudinal axis of the bundle. Disposed on at least one of the probe elements is an interface element. The interface element is coupled to a communication element, which communicates a signal between the interface element and another point in the multi-element probe array.

BRIEF DESCRIPTION OF THE DRAWINGS

The present invention will become more fully apparent from the following description and appended claims, taken in conjunction with the accompanying drawings. Understanding that these drawings merely depict exemplary embodiments of the present invention they are, therefore, not to be considered limiting of its scope. It will be readily appreciated that the components of the present invention, as generally described and illustrated in the figures herein, can be arranged and designed in a wide variety of different configurations. Nonetheless, the invention will be described and explained with additional specificity and detail through the use of the accompanying drawings in which:

FIGS. 3-11 illustrate front views of a variety of arrangements of probe elements and spacer elements in a multi-element probe array in accordance with embodiments of the present invention;

DETAILED DESCRIPTION OF EXEMPLARY EMBODIMENTS

Figure 1:
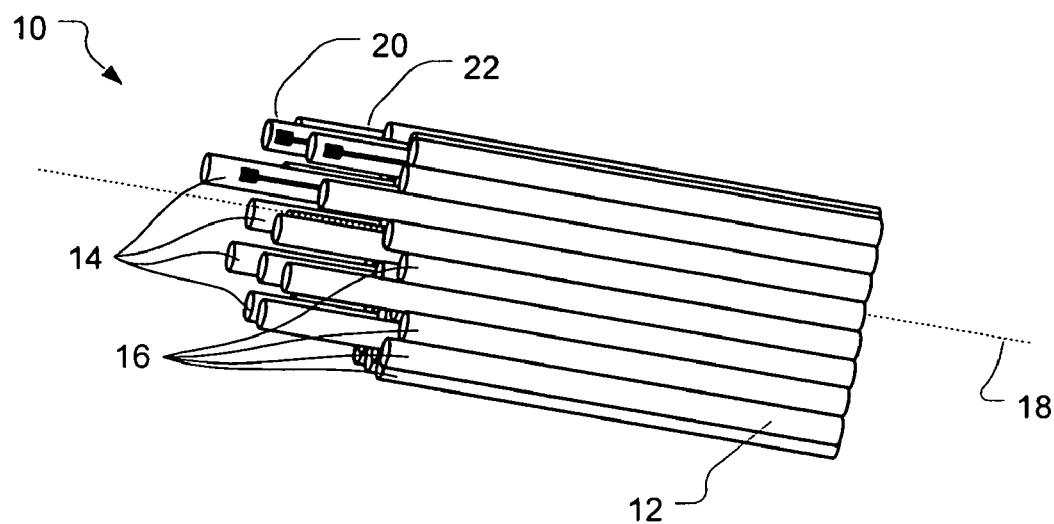
FIG. 1 illustrates a perspective view of a multi-element probe array in accordance with a first embodiment of the present invention.

The following detailed description of exemplary embodiments of the invention makes reference to the accompanying drawings, which form a part hereof and in which are shown, by way of illustration, exemplary embodiments in which the invention may be practiced. While these exemplary embodiments are described in sufficient detail to enable those skilled in the art to practice the invention, it should be understood that other embodiments may be realized and that various changes to the invention may be made without departing from the spirit and scope of the present invention. Thus, the following more detailed description of the embodiments of the present invention is not intended to limit the scope of the invention, as claimed, but is presented for purposes of illustration only and not limitation to describe the features and characteristics of the present invention, to set forth the best mode of operation of the invention, and to sufficiently enable one skilled in the art to practice the invention. Accordingly, the scope of the present invention is to be defined solely by the appended claims.

The following detailed description and exemplary embodiments of the invention will be best understood by reference to the accompanying drawings, wherein the elements and features of the invention are designated by numerals throughout.

In describing the present invention, the following terminology will be used. The singular forms "a,""an," and "the" include plural referents unless the context clearly dictates otherwise. Thus, for example, reference to a microfilament includes reference to one or more microfilament.

As used herein, the term "about" means quantities, dimensions, sizes, formulations, parameters, shapes and other characteristics need not be exact, but may be approximated and/or larger or smaller, as desired, reflecting acceptable tolerances, conversion factors, rounding off, measurement error and the like and other factors known to those of skill in the art.

Numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to 5" should be interpreted to include not only the explicitly recited values of about 1 to 5, but also include individual values and sub-ranges within the indicated range. Thus, included in this numerical range are individual values such as 2, 3, and 4 and sub-ranges such as 1-3, 2-4, and 3-5, etc. This same principle applies to ranges reciting only one numerical value and should apply regardless of the breadth of the range or the characteristics being described.

As used herein, a plurality of items may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

With reference to FIG. 1, shown is an illustration of a multi-element probe array according to a first exemplary embodiment of the present invention. Specifically, FIG. 1 illustrates the multi-element probe array 10 as including a plurality of microfibers 12 extending longitudinally and oriented substantially parallel to form a bundle. A first subset of the plurality of microfibers defines probe elements 14 and a second subset of the plurality of microfibers defines spacer elements 16. The front end of at least one of the probe elements is displaced in a forward position along a longitudinal axis 18 of the bundle. It will be understood that, although shown as straight, the longitudinal axis may curve or bend, as flexible microfilaments can be used in embodiments of the present invention.

Disposed on at least one of the probe elements is an interface element 20. The interface element is connected to a communication element 22, also disposed on the probe element. The communication element communicates a signal between the interface element and another point in the multi-element probe array.

The microfibers 12 can be, for example, a glass fiber, a silicon fiber, or a microwire. Although shown here as having a round cross section, the microfibers can have a round, oval, triangular, rectangular, hexagonal, octagonal, polygonal, or a generally arbitrary cross section. For example, various ways are known to draw a glass fiber having a desired cross section. One or more of the microfibers can have a longitudinally oriented bore. Very thin microfibers can be used, including for example microfibers having a cross-sectional diameter of less than 50 micrometers, including for example a cross-sectional diameter of 12 micrometers. Microfibers can be chosen to have desirable strength and flexibility properties, helping to avoid overly brittle or stiff probes.

A plurality of probe elements 14 can be defined by microfibers for which the front ends extend forward relative to other microfibers. The tips 24 of the probe element may be sharpened, for example, by cutting the probe tip at an angle or by etching the prove tip or similar techniques.

Microfibers are used for both the probe elements 14 and the spacer elements. Accordingly, great design freedom is achieved in the arrangement of the multi-element probe array 10. Many options for the length of the probe elements are available. For example, probe elements can have a large variety of different lengths, as illustrated in FIG. 1. As another example, probe elements can all extend substantially the same length relative to the spacer elements. As yet another example, several groups of probe elements can each have a common length, the length for each group different from the other groups.

Figure 2:
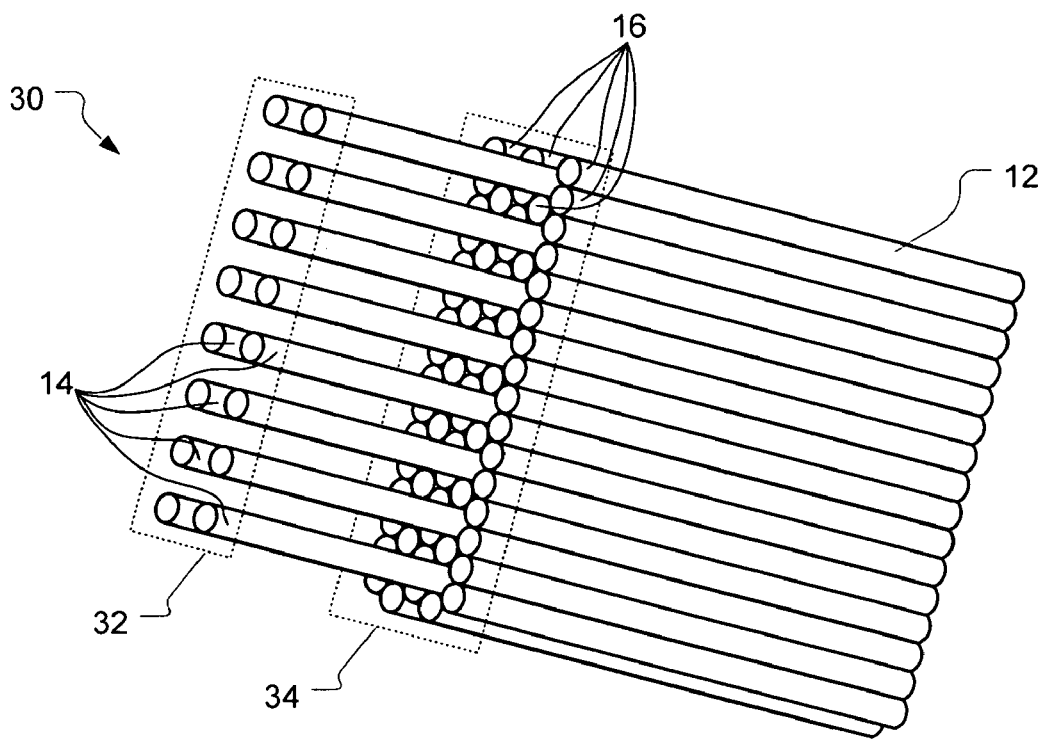
FIG. 2 illustrates a perspective view of a multi-element probe array in accordance with a second embodiment of the present invention.

For example, FIG. 2 illustrates a multi-element probe array 30 where the probe elements 14 all extend to a substantially same position along the longitudinal axis 18 to define a first plane 32 in accordance with another embodiment of the present invention. Similarly, the spacer elements 16 all extend to a substantially same longitudinal position, different from the probe elements, to define a second plane 34, such that the length of the probe elements are all equal. Accordingly, many options as to the longitudinal lengths of the probe elements are possible with different embodiments of the present invention.

Great flexibility in the axial positioning of probe elements 14 is also obtained. Probe elements can be positioned regularly or irregularly. For example, FIGS. 3-11 illustrate several different arrangements of a multi-element probe in cross sectional view, in accordance with embodiments of the present invention. The spacer elements 16 and probe elements 14 are shown with different cross hatching.

FIGS. 3-6, illustrate microfibers are arranged in a hexagonal close packed array. In FIG. 3, probe elements are disposed irregularly, and in FIGS. 4-6, probe elements are disposed regularly, using differing arrangements.

The microfibers can also be positioned in other arrangements, as illustrated in FIGS. 7-10. The microfibers need not all be similar in cross section, either shape or size, as illustrated in FIG. 11. For example, circular, triangular, square, hexagonal, and other cross sectional shapes can be used.

The multi-element probe array 10 is also scalable in size. The multi-element probe array can include a small number of probe elements, for example, three or more probe elements. As another example, the multi-element probe array can include a large number of probe elements, for example 1,000 or more. As another example, a multi-element probe array having 10,000 probe elements in a 100×100 array can be constructed using the arrangement of FIG. 6 using about 40,000 microfibers. Using microfibers of about 12 micron diameter, the individual probes are spaced about 24microns apart. The entire array has overall dimensions of about 2.5 millimeter by about 2.5 millimeter. Accordingly, the multi-element probe array can prove suitable for use in interfacing to a nerve bundle or brain region while providing high resolution to allow mapping of individual nerves or nerve control regions.

Another benefit of the microfiber-based construction of the multi-element probe array 10 is provided by the relatively large number of spacer elements included within the array. For example, in FIG. 5, approximately twice as many spacer elements 16 are included as probe elements 14. In FIG. 6, approximately three times as many spacer elements are included as probe elements. These spacer elements can be used for communication elements or to support electronic circuitry as described below.

Figure 12:
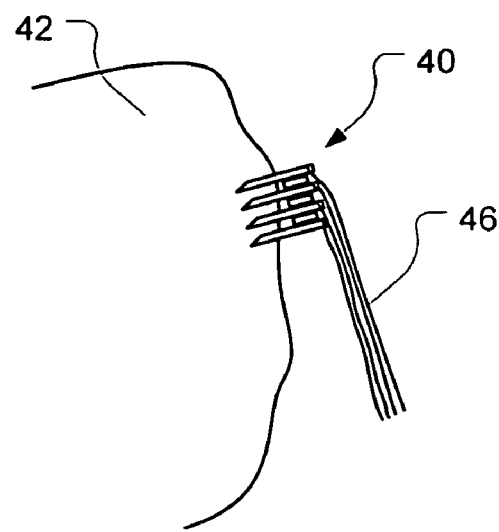
FIG. 12 illustrates a side view of a brain probe application of a multi-element probe array according to another exemplary embodiment of the present invention.

Various configurations of the multi-element probe array can prove suitable for different uses. For example, FIG. 12 illustrates a multi-element probe array 40 suitable for use as a probe into brain tissue 42 in accordance with an embodiment of the present invention. As described above, the multi-element probe array includes a plurality of probe elements 14 separated by a plurality of spacer elements 16. Interface elements 20 on the probe elements are connected via a communication element 22 to the rear 44 of the multi-element probe array. Microwires or optical fibers 46 are connected to the rear of the multi-element probe array and exit at approximately a right angle relative to the longitudinal axis of the bundle. The microwires or optical fibers allow connection between the multi-element probe array and another piece of equipment (not shown), for example a connector disposed on the end of the cable.

Figure 13:
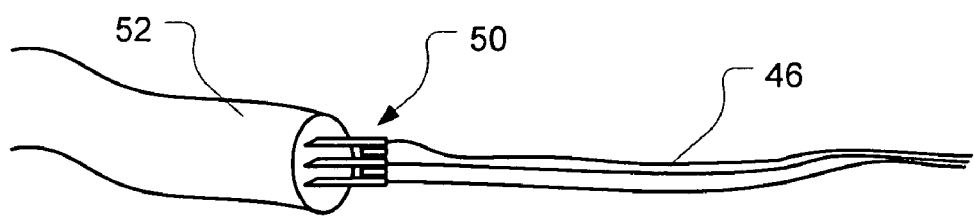
FIG. 13 illustrates a side view of a nerve probe application of a multi-element probe array according to another exemplary embodiment of the present invention.

As another example, FIG. 13 illustrates a multi-element probe array 50 suitable for use as a probe into nerve tissue 52 in accordance with an embodiment of the present invention. Construction is similar to that of FIG. 12, except that microwires or optical fibers 46 exit the rear of the multi-element probe array approximately in line with the longitudinal axis of the bundle. The nerve probe can prove suitable, for example, for providing direct interface to an artificial limb.

Turning to the interface elements 20 in further detail, various different interface element arrangements can be used in a multi-element probe array in accordance with embodiments of the present invention. The interface element can be designed for sensing, (e.g., accepting an electronic signal) or for stimulus (e.g., outputting an electronic signal) or for both. For example, the interface element can be an electronic sensor, an optical sensor, or a chemical sensor. More particularly, the interface element can be a conductive electrode for transferring an electrical signal between the probe element and the medium into which the probe element is inserted. As another example, the interface element can include active electronic circuitry microfabricated onto the probe element. For example, the interface element can be a photodiode, phototransistor, light emitting diode, light emitting transistor, and the like. As yet another example, the interface element can be a chemical sensing micro-cantilever.

The communication element 22 can be configured for electrical, optical, or fluid communication. For example, the communication element can be an electrically conductive strip disposed along the probe element. The communication element can include connections or couplings between different microfibers as discussed further below. For example, an electrically conductive strip can be microfabricated onto the microfiber which forms the probe element. As another example, the communication element can be a conductive microwire positioned as a spacer element. As another example, the communication element can be an optical waveguide. For example, the microfiber can be an optical fiber, or the microfiber can have an optical waveguide microfabricated thereon. As yet another example, the communication element can be a fluid communication channel, for example provided by a bore through the corresponding microfilament. A fluid communication channel can be used, for example, for extracting a sample of fluid or injecting a chemical compound or assay. Combinations of electrically, optically, and/or fluid communicating elements can be included in the multi-element probe array.

As mentioned above, active electronic circuitry can be included in the multi-element probe array. Active electronic circuitry can be microfabricated onto the probe elements or spacer elements using cylindrical lithography, for example as described in commonly-owned U.S. Pat. Nos. 5,106,455, 5,269,882, and 5,273,622 to Jacobsen et al., herein incorporated by reference. Active electronics can include amplifiers, attenuators, multiplexers, demultiplexers, wireless transmitters, wireless receivers, wireless transceivers, and the like. For example, multiplexers and demultiplexers can be used to combine multiple signals for input and output from the multi-element probe array as discussed further below, providing benefits in reduced interconnection requirements.

As yet another example, the active electronic circuitry can include a wireless transmitter and receiver. For example, a multi-element probe array can be integrated with a wireless transmitter and receiver and power source, and be entirely contained subcutaneously. Avoiding the placement of a wired connection between the multi-element probe array and other equipment can help to avoid the need for transcutaneous wires which can present a site for infection and other difficulties.

Figure 14:
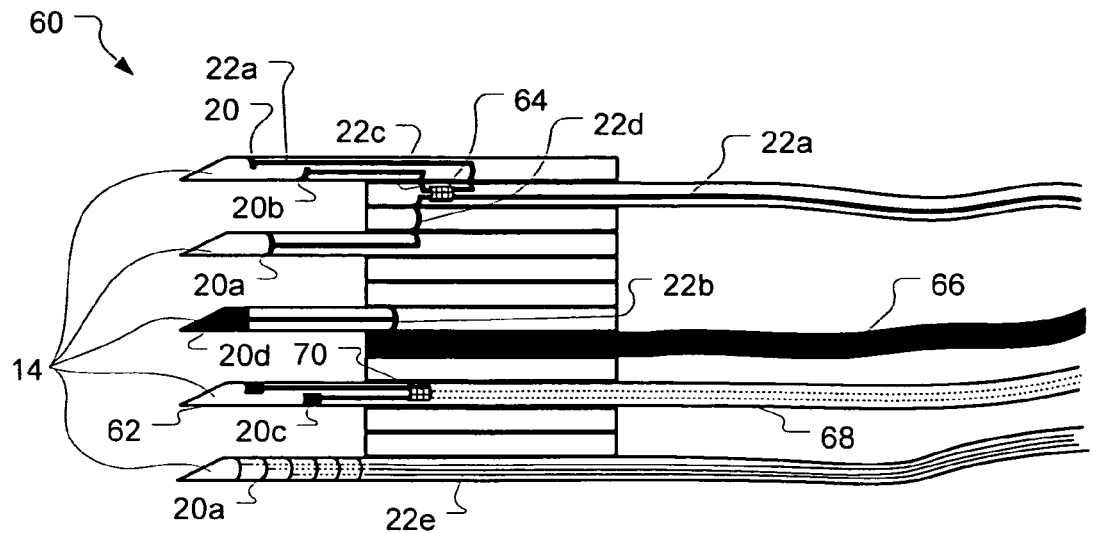
FIG. 14 illustrates a side view of a multi-element probe array illustrating a variety of interface element and communication element arrangements in accordance with embodiments of the present invention.

FIG. 14 illustrates a multi-element probe array in accordance with another embodiment of the present invention showing various configurations of interface elements and communication elements. Although several different configurations are shown, it will be understood that these arrangement need not be used at the same time. Other combinations and arrangements will become apparent from the following discussion.

The multi-element probe array 60 includes a linear bundle of microfibers 12 oriented along a longitudinal axis 18 having front ends 62 positioned differentially along the longitudinal axis. A most forward positioned subset of the microfibers defines probe elements 14. The probe elements can have interface elements 20 disposed near their front ends. Communication elements 22 are disposed on the microfibers and operatively coupled to the interface elements.

Individual probe elements 14 can have zero, one or more interface elements 20. Including multiple interface elements can prove helpful in avoiding a need to place a probe in a precise location. For example, in application as a brain probe, a multi-element probe array may be placed in a general location associated with a desired brain function (e.g., a localized area associated with motor control of a particular limb). The combination of a large number of probe elements each having a large number of interface elements, provides very high resolution sampling of brain function within the three-dimensional area spanned by the probe elements. For example, a 10,000 probe element array, as discussed above, having 100 interface elements on each probe element, can provide 1 million sample points. Brain function can be mapped in order to determine the appropriate combinations of probe elements corresponding to a particular desired stimulus or response. For example, the brain probe can prove suitable for use in interfacing a prosthesis, such as an artificial limb or eye, directly to the appropriate brain regions for controlling the prosthesis. Similarly, a nerve probe can prove suitable for use in interfacing to a nerve bundle, for example at the end of an amputated limb.

Interface elements 20 can take on various geometries. For example, an electrical interlace element can be provided by variously shaped conductive regions disposed on the probe element 14. For example, small rings 20*a*, partial rings 20*b* or patches 20*c* can be used. As another example, an entire tip 20*d* of the probe element can be coated with conductive material to form the interface element.

Signals are inserted or extracted from the interface elements via the communication elements 22. The communication elements couple signals between the interface elements and points rearward in the bundle of microfibers. For example, the communication elements may couple signals between the interface elements and a connector.

Multiple rings 20*a* can be included on a single probe element, each ring connected to a corresponding one of multiple communication elements 22*e* to create plural interface elements on a single probe element. For example, multiple conductive strips can be deposited on the outer surface of the probe element, insulating material placed over the conductive strips, portions of the insulating material etched away to expose the conductive strips, and conductive rings deposited so that each ring makes electrical contact to a corresponding conductive strip A communication element 20 can connect to circuitry 64 disposed on the microfiber. For example, the circuitry can be a multiplexer (or demultiplexer) which is coupled to several interface elements 20. This can allow multiple signals to be combined onto a single communication element 22, helping to reduce the number of interconnections between the probe and other equipment. Various techniques for multiplexing/demultiplexing can be used in embodiments of the present invention.

Communication elements can also include conductive strips 22a, rings 22b, partial rings 22c, and similar geometries microfabricated on the microfilaments. For example, connection between communication elements on adjacent microfilaments can be provided by conductive patches 22d positioned at the same longitudinal position along the axis of the bundle. Alternately, communication elements can be provided by a microwire 66 or optical fiber 68. For example, an electrical signal can be coupled into or out of the probe element by providing electrical connection from an interface element 20d to an adjacent microfiber which is a conductive microwire 66. As another example, an optical signal can input or output using active circuitry 70 coupled into or out of an optical fiber 68.

Figure 15:
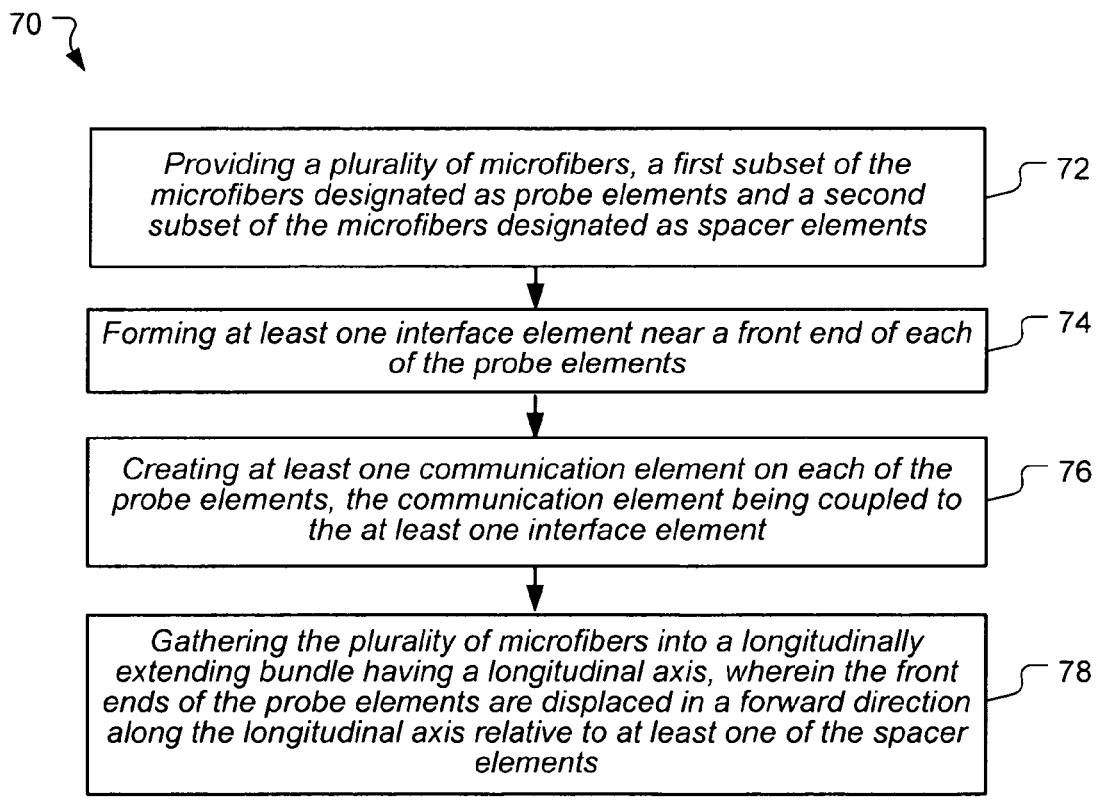
FIG. 15 illustrates a flow diagram of a method of making a multi-element probe array in accordance with an embodiment of the present invention.

Finally, a method of making a multi-element probe array will now be described. The method 70, illustrated in flow diagram form in FIG. 15, includes providing 72 a plurality of microfibers. A first subset of the microfibers is designated as probe elements and a second subset of the microfibers is designated as spacer elements. Various types of microfibers can be provided, as described above. Another step of the method is forming 74 at least one interface element near a front end of each of the probe elements. For example, interface elements can be deposited using cylindrical lithography, and can have various geometries as described above. Another step is creating 76 at least one communication element on each of the probes so that the interface element and communication element are coupled together. As discussed above, a large variety of configurations of the interface element can be created, for example using cylindrical lithography. Finally, the method includes gathering 78 the plurality of microfibers into a longitudinally extending bundle. Front ends of the probe elements are displaced in a forward direction relative to the spacer elements along a longitudinal axis of the bundle, for example as described above. The method can also include fixing the plurality of microfilaments together over at least a portion of their length. For example, the spacer elements and probe elements can be fixed together near an end of the bundle to hold the probe elements in their displaced position relative to the spacer elements. The bundle can also be fixed together along its entire length, or can be fixed together at intervals along its length.

Various techniques can be used to gather the microfilaments together to form the bundles. For example, the bundle can be stacked up by placing a first microfiber in a manufacturing jig, and then adding additional microfibers on top of or along side of previously placed elongate cylindrical elements and sliding the microfibers along until a stop in the manufacturing jig is reached. The manufacturing jig can thus include a set of stops that define the displaced forward positions of the probe elements.

Alternately, the ends of the microfibers can initially be disposed in a common plane, and then the spacer elements preferentially etched to expose the probe elements. For example, this can be accomplished by using different materials for the probe elements and the spacer elements, or by depositing etch-resist on the probe elements before forming the bundle.

Summarizing and reiterating to some extent, it can be appreciated from the foregoing that embodiments of the present invention can provide a multi-element probe array having a number of benefits. A multi-element probe array as taught herein can be used to provide a large number of interfacing elements within a three dimensional volume. Probe elements can include large numbers of interfacing elements, helping to avoid a need to precisely position the individual probe elements. A high degree of flexibility in the configuration of the multi-element probe array is provided by constructing the multi-element probe array using a plurality of microfibers. For example, individual microfibers can serve as active probe elements, spacer elements, or communication elements. Different microfiber types can be used to provide desired properties, including mixing different types and shapes of microfibers within a multi-element probe array. Although biomedical applications of the multi-element probe array for brain and nerve interface have been described in some detail, various other applications will be apparent from the foregoing.

The foregoing detailed description describes the invention with reference to specific exemplary embodiments. However, it will be appreciated that various modifications and changes can be made without departing from the scope of the present invention as set forth in the appended claims. The detailed description and accompanying drawings are to be regarded as merely illustrative, rather than as restrictive, and all such modifications or changes, if any, are intended to fall within the scope of the present invention as described and set forth herein.

More specifically, while illustrative exemplary embodiments of the invention have been described herein, the present invention is not limited to these embodiments, but includes any and all embodiments having modifications, omissions, combinations (e.g., of aspects across various embodiments), adaptations and/or alterations as would be appreciated by those in the art based on the foregoing detailed description. The limitations in the claims are to be interpreted broadly based the language employed in the claims and not limited to examples described in the foregoing detailed description or during the prosecution of the application, which examples are to be construed as non-exclusive. For example, in the present disclosure, the term "preferably" is non-exclusive where it is intended to mean "preferably, but not limited to." Any steps recited in any method or process claims may be executed in any order and are not limited to the order presented in the claims. Means-plus-function or step-plus-function limitations will only be employed where for a specific claim limitation all of the following conditions are present: a) "means for" or "step for" is expressly recited in that limitation; b) a corresponding function is expressly recited in that limitation; and c) structure, material or acts that support that function are described within the specification. Accordingly, the scope of the invention should be determined solely by the appended claims and their legal equivalents, rather than by the descriptions and examples given above.

What is claimed is:

1. A multi-element probe array useable as a sensor and/or for applying a stimulus comprising:
   a plurality of microfibers extending longitudinally and oriented substantially parallel to form a bundle having a longitudinal axis, each of the plurality of microfibers having a front end, a first subset of the plurality of microfibers defining probe elements and a second subset of the plurality of microfibers defining spacer elements, wherein the front ends of at least one of the probe elements is displaced in a forward position along the longitudinal axis relative to at least one of the spacer elements;

an interface element disposed on at least one of the probe elements; and a communication element disposed on at least one of the probe elements and operatively coupled to at least one of the interface elements and configured to communicate a signal between the interface element and another point in the multi-element probe array.

2. The multi-element probe array of claim 1, wherein the plurality of microfibers are oriented in a hexagonal close pack.

3. The multi-element probe array of claim 1, wherein the front ends of the spacer elements are at a substantially same longitudinal position so as to define a plane.

4. The multi-element probe array of claim 3, wherein the front ends of the probe elements are displaced a substantially equal distance relative to the plane.

5. The multi-element probe array of claim 1, wherein at least one of the probe elements has a sharpened tip.

6. The multi-element probe array of claim 1, wherein at least one of the plurality of microfibers is a material selected from the group consisting of a glass fiber, a silicon fiber, and a microwire.

7. The multi-element probe array of claim 1, wherein at least one of the plurality of microfibers has a cross section shape chosen from the group consisting of round, triangular, rectangular, hexagonal, and octagonal.

8. The multi-element probe array of claim 1, wherein at least one of the plurality of microfibers has a longitudinally oriented bore.

9. The multi-element probe array of claim 1, wherein each of the plurality of microfibers has a cross-sectional diameter of less than 50 micrometers.

10. The multi-element probe array of claim 1, comprising at least 1000 microfibers.

11. The multi-element probe array of claim 1, wherein the interface element is chosen from the group of sensors consisting of an electronic sensor, an optical sensor, and a chemical sensor.

12. The multi-element probe array of claim 1, wherein the interface element is chosen from the group of stimulators consisting of an electrode, a phototransistor, a photodiode, and a laser.

13. The multi-element probe array of claim 1, wherein the interface element comprises active electronics circuitry.

14. The multi-element probe array of claim 13, wherein the active electronics circuitry is chosen from the group consisting of a photodiode, a phototransistor, a light emitting diode, a light emitting transistor, a laser, a transistor, an amplifier, and an attenuator.

15. The multi-element probe array of claim 1, wherein the communication element is an electrically conductive strip.

16. The multi-element probe array of claim 1, wherein the communication element is provided by the microfiber.

17. The multi-element probe array of claim 16, wherein the communication element is chosen from the group consisting of an optical fiber and a microwire.

18. The multi-element probe array of claim 1, wherein the communication element is a conductive ring circumscribing the microfiber.

19. The multi-element probe array of claim 1, wherein the at least one probe element further comprises
    a plurality of interface elements disposed on the least one probe element; and
    a plurality of communication elements disposed on the at least one probe element, each communication element operatively coupled to a corresponding interface element and configured to communicate a signal between the interface element and another point in the multi-element probe array.

20. The multi-element probe array of claim 1, wherein the spacer elements further comprise electronic circuitry coupled to the probe elements.

21. The multi-element probe array of claim 20, wherein the electronic circuitry comprises multiplexing circuitry configured to combine a plurality of signals transmitted between the interface elements and a signal path element disposed on one of the plurality of microfibers.

22. The multi-element probe array of claim 21, further comprising a microwire coupled to the signal path element.

23. A method of making a multi-element probe array comprising the steps of:
    a.) providing a plurality of microfibers, a first subset of the microfibers designated as probe elements and a second subset of the microfibers designated as spacer elements;
    b.) forming at least one interface element near a front end of each of the probe elements;
    c.) creating at least one communication element on each of the probe elements, the communication element being coupled to the at least one interface element; and
    d.) gathering the plurality of microfibers into a longitudinally extending bundle having a longitudinal axis, wherein the front ends of the probe elements are displaced in a forward direction along the longitudinal axis relative to at least one of the spacer elements.

24. The method of claim 23, further comprising utilizing cylindrical lithography to form the at least one communication element on each of the probe elements, and to create the at least one communication element on each of probe elements.

25. The method of claim 23 further comprising fixing the plurality of microfibers together over at least a portion of their length.

* * * * *